US006825461B2

(12) United States Patent
Guevremont et al.

(10) Patent No.: US 6,825,461 B2
(45) Date of Patent: *Nov. 30, 2004

(54) FAIMS APPARATUS AND METHOD WITH ION DIVERTING DEVICE

(75) Inventors: Roger Guevremont, Gloucester (CA); Randy Purves, Gloucester (CA)

(73) Assignee: National Research Council Canada, Ottawa (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/221,481

(22) PCT Filed: Mar. 14, 2001

(86) PCT No.: PCT/CA01/00309

§ 371 (c)(1),
(2), (4) Date: Sep. 13, 2002

(87) PCT Pub. No.: WO01/69217

PCT Pub. Date: Sep. 20, 2001

(65) Prior Publication Data

US 2003/0150985 A1 Aug. 14, 2003

Related U.S. Application Data

(60) Provisional application No. 60/189,085, filed on Mar. 14, 2000.

(51) Int. Cl.[7] .................................................. H01J 49/00
(52) U.S. Cl. ........................ 250/287; 250/282; 250/288
(58) Field of Search ................................ 250/281–300, 250/201–238

(56) References Cited

U.S. PATENT DOCUMENTS

| | | | | |
|---|---|---|---|---|
| 5,420,424 A | * | 5/1995 | Carnahan et al. | 250/287 |
| 6,495,823 B1 | * | 12/2002 | Miller et al. | 250/286 |
| 6,504,149 B2 | * | 1/2003 | Guevremont et al. | 250/286 |
| 6,512,224 B1 | * | 1/2003 | Miller et al. | 250/286 |
| 6,621,077 B1 | | 9/2003 | Guevremont et al. | |
| 6,639,212 B1 | | 10/2003 | Guevremont et al. | |
| 2003/0057367 A1 | | 3/2003 | Guevremont et al. | |
| 2003/0213899 A9 | * | 11/2003 | Guevremont et al. | 250/281 |

FOREIGN PATENT DOCUMENTS

| | | |
|---|---|---|
| WO | WO 00/08454 A1 | 2/2000 |
| WO | WO 00/08455 A1 | 2/2000 |
| WO | WO 00/08456 A1 | 2/2000 |
| WO | WO 00/08457 A1 | 2/2000 |

OTHER PUBLICATIONS

U.S. patent application Ser. No. 09/762,239, Guevremont et al., filed Jun. 28, 2001.
U.S. patent application Ser. No. 09/762,238, Guevremont et al., filed May 9, 2001.
Buryakov et al., "A new method of separation of multi-atomic ions by mobility at atmospheric pressure using a high-frequency amplitude-asymmetric strong electric field", Int. J. Mass Spectrom. Ion Proc., vol. 128, pp 143–148, 1993.
Carnahan et al., "Field Ion Spectrometry—A New Analytical Technology for Trace Gas Analysis" Proceedings of the Annual ISA Analysis Division Symposium, No. 29, Apr. 1996, pp. 85–94, Apr. 1996.

(List continued on next page.)

Primary Examiner—Nikita Wells
Assistant Examiner—Christopher M. Kalivoda
(74) Attorney, Agent, or Firm—Freedman & Associates

(57) ABSTRACT

A method and an apparatus for selectively transmitting ions using a FAIMS analyzer is disclosed. An ion diverter is included within the FAIMS analyzer for affecting the trajectories of ions after separation to direct the ions in a known fashion. The ion diverter is optionally a gas flow source or an electrode for generating an electrical field to alter ion flow.

34 Claims, 8 Drawing Sheets

OTHER PUBLICATIONS

Guevremont et al., "Atmospheric Pressure Ion Focusing in a High–Field Asymmetric Waveform ion Mobility Spectrometer" Review of Scientific Instruments, Institute of Physics, vol. 70, No. 2, Feb. 1999 (New York, USA).

Guevremont et al., "Ion Trapping at Atmospheric Pressure (760 Torr) and Room Temperature with High–Field Asymmetric Waveform Ion Mobility Spectrometer", Int'l Journal of Mass Spectrometry, v. 193, pp. 45–56, 1999.

Purves et al., "Mass Spectrometric Characterization of a High–Field Asymmetric Waveform Ion Mobility Spectrometer", Review of Scientific Instruments, American Institute of Physics, vol. 69, No. 12, Dec. 1998 (New York, USA).

* cited by examiner

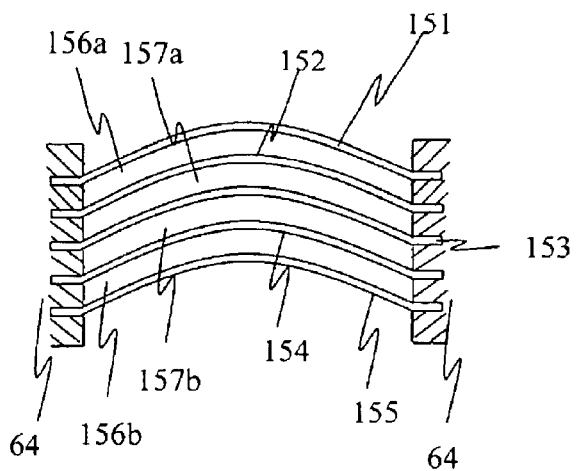
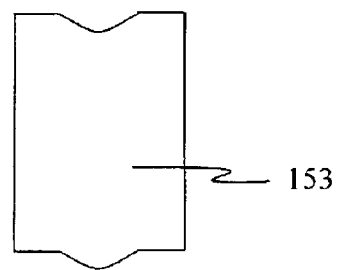
Figure 5a Figure 5b
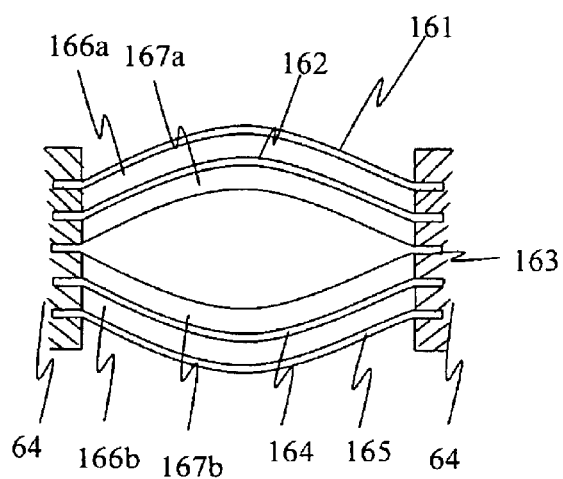
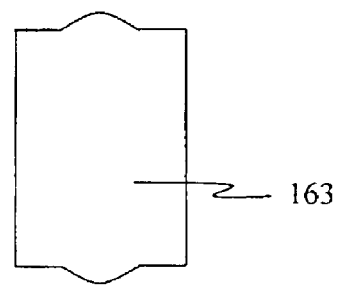
Figure 6a Figure 6b

FAIMS APPARATUS AND METHOD WITH ION DIVERTING DEVICE

This application claims the benefit of U.S. Provisional Patent application No. 60/189,085 filed Mar. 14, 2000.

FIELD OF THE INVENTION

The present invention relates to an apparatus and method for separating ions, more particularly the present invention relates to an apparatus and method for separating ions based on the ion focusing principles of high field asymmetric waveform ion mobility spectrometry (FAIMS).

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are gated into the drift tube and are subsequently separated in dependence upon differences in their drift velocity. The ion drift velocity is proportional to the electric field strength at low electric field strength, for example 200 V/cm, and the mobility, K, which is determined from experimentation, is independent of the applied electric field. Additionally, in IMS the ions travel through a bath gas that is at sufficiently high pressure such that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied field, and K becomes dependent upon the applied electric field. At high electric field strength, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry. Ions are separated in FAIMS on the basis of a difference in the mobility of an ion at high field strength, $K_h$, relative to the mobility of the ion at low field strength, K. In other words, the ions are separated because of the compound dependent behavior of $K_h$ as a function of the applied electric field strength. FAIMS offers a new tool for atmospheric pressure gas-phase ion studies since it is the change in ion mobility, and not the absolute ion mobility, that is being monitored.

The principles of operation of FAIMS using flat plate electrodes have been described by I. A. Buryakov, E. V. Krylov, E. G. Nazarov and U. Kh. Rasulev in a paper published in the International Journal of Mass Spectrometry and Ion Processes; volume 128 (1993), pp. 143–148, the contents of which are herein incorporated by reference. The mobility of a given ion under the influence of an electric field is expressed by: $K_h=K(1+f(E))$, where $K_h$ is the mobility of an ion at high electrical field strength, K is the coefficient of ion mobility at low electric field strength and f(E) describes the functional dependence of the ion mobility on the electric field strength. Ions are classified into one of three broad categories on the basis of a change in ion mobility as a function of the strength of an applied electric field, specifically: the mobility of type A ions increases with increasing electric field strength; the mobility of type C ions decreases; and, the mobility of type B ions increases initially before decreasing at yet higher field strength. The separation of ions in FAIMS is based upon these changes in mobility at high electric field strength. Consider an ion, for example a type A ion, which is being carried by a gas stream between two spaced-apart parallel plate electrodes of a FAIMS device. The space between the plates defines an analyzer region in which the separation of ions occurs. The net motion of the ion between the plates is the sum of a horizontal x-axis component due to the flowing stream of gas and a transverse y-axis component due to the electric field between the parallel plate electrodes. The term "net motion" refers to the overall translation that the ion, for instance said type A ion, experiences, even when this translational motion has a more rapid oscillation superimposed upon it. Often, a first plate is maintained at ground potential while the second plate has an asymmetric waveform, V(t), applied to it. The asymmetric waveform V(t) is composed of a repeating pattern including a high voltage component, $V_1$, lasting for a short period of time $t_2$ and a lower voltage component, $V_2$, of opposite polarity, lasting a longer period of time $t_1$. The waveform is synthesized such that the integrated voltage-time product, and thus the field-time product, applied to the plate during each complete cycle of the waveform is zero, for instance $V_1t_2+V_2t_1=0$; for example +2000 V for 10 $\mu$s followed by −1000 V for 20 $\mu$s. The peak voltage during the shorter, high voltage portion of the waveform is called the "dispersion voltage" or DV in this disclosure.

During the high voltage portion of the waveform, the electric field causes the ion to move with a transverse y-axis velocity component $v_1=K_hE_{high}$, where $E_{high}$ is the applied field, and $K_h$ is the high field ion mobility under ambient electric field, pressure and temperature conditions. The distance traveled is $d_1=v_1t_2=K_hE_{high}t_2$, where $t_2$ is the time period of the applied high voltage. During the longer duration, opposite polarity, low voltage portion of the asymmetric waveform, the y-axis velocity component of the ion is $v_2=KE_{low}$, where K is the low field ion mobility under ambient pressure and temperature conditions. The distance traveled is $d_2=v_2t_1=KE_{low}t_1$. Since the asymmetric waveform ensures that $(V_1\ t_2)+(V_2\ t_1)=0$, the field-time products $E_{high}t_2$ and $E_{low}t_1$ are equal in magnitude. Thus, if $K_h$ and K are identical, $d_1$ and $d_2$ are equal, and the ion is returned to its original position along the y-axis during the negative cycle of the waveform, as would be expected if both portions of the waveform were low voltage. If at $E_{high}$ the mobility $K_h>K$, the ion experiences a net displacement from its original position relative to the y-axis. For example, positive ions of type A travel farther during the positive portion of the waveform, for instance $d_1>d_2$, and the type A ion migrates away from the second plate. Similarly, positive ions of type C migrate towards the second plate.

If a positive ion of type A is migrating away from the second plate, a constant negative dc voltage can be applied to the second plate to reverse, or to "compensate" for, this transverse drift. This dc voltage, called the "compensation voltage" or CV in this disclosure, prevents the ion from migrating towards either the second or the first plate. If ions derived from two compounds respond differently to the applied high strength electric fields, the ratio of $K_h$ to K may be different for each compound. Consequently, the magnitude of the CV necessary to prevent the drift of the ion toward either plate is also different for each compound. Thus, when a mixture including several species of ions is being analyzed by FAIMS, only one species of ion is selectively transmitted for a given combination of CV and DV. The remaining species of ions, for instance those ions that are other than selectively transmitted through FAIMS, drift towards one of the parallel plate electrodes of FAIMS and are neutralized. Of course, the speed at which the remaining species of ions move towards the electrodes of FAIMS depends upon the degree to which their high field mobility properties differ from those of the ions that are selectively transmitted under the prevailing conditions of CV and DV.

An instrument operating according to the FAIMS principle as described previously is an ion filter, capable of selective transmission of only those ions with the appropriate ratio of $K_h$ to K. In one type of experiment using FAIMS devices, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained. It is a significant limitation of early FAIMS devices, which used electrometer detectors, that the identity of peaks appearing in the CV spectrum are other than unambiguously confirmed solely on the basis of the CV of transmission of a species of ion. This limitation is due to the unpredictable, compound-specific dependence of $K_h$ on the electric field strength. In other words, a peak in the CV spectrum is easily assigned to a compound erroneously, since there is no way to predict or even to estimate in advance, for example from the structure of an ion, where that ion should appear in a CV spectrum. In other words, additional information is necessary in order to improve the likelihood of assigning correctly each of the peaks in the CV spectrum. For example, subsequent mass spectrometric analysis of the selectively transmitted ions greatly improves the accuracy of peak assignments of the CV spectrum.

In U.S. Pat. No. 5,420,424 which issued on May 30 1995, B. L. Carnahan and A. S. Tarassov disclose an improved FAIMS electrode geometry in which the flat plates that are used to separate the ions are replaced with concentric cylinders, the contents of which are herein incorporated by reference. The concentric cylinder design has several advantages, including higher sensitivity compared to the flat plate configuration, as was discussed by R. W. Purves, R. Guevremont, S. Day, C. W. Pipich, and M. S. Matyjaszczyk in a paper published in Reviews of Scientific Instruments; volume 69 (1998), pp 4094–4105. The higher sensitivity of the cylindrical FAIMS is due to a two-dimensional atmospheric pressure ion focusing effect that occurs in the analyzer region between the concentric cylindrical electrodes. When no electrical voltages are applied to the cylinders, the radial distribution of ions should be approximately uniform across the FAIMS analyzer. During application of DV and CV, however, the radial distribution of ions is not uniform across the annular space of the FAIMS analyzer region. Advantageously, with the application of an appropriate DV and CV for an ion of interest, those ions become focused into a band between the electrodes and the rate of loss of ions, as a result of collisions with the FAIMS electrodes, is reduced. The efficiency of transmission of the ions of interest through the analyzer region of FAIMS is thereby improved as a result of this two-dimensional ion focusing effect.

The focussing of ions by the use of asymmetric waveforms has been discussed above. For completeness, the behavior of those ions that are not focussed within the analyzer region of a cylindrical geometry FAIMS is described here, briefly. As discussed previously, those ions having high field ion mobility properties that are other than suitable for focussing under a given set of DV, CV and geometric conditions will drift toward one or another wall of the FAIMS device. The rapidity with which these ions move towards the wall depends on the degree to which their $K_h/K$ ratio differs from that of the ion that is transmitted selectively under the prevailing conditions. At the very extreme, ions of completely the wrong property, for instance a type A ion versus a type C ion, are lost to the walls of the FAIMS device very rapidly.

The loss of ions in FAIMS devices should be considered one more way. If an ion of type A is focussed, for example at DV 2500 volts, CV–11 volts in a given geometry, it would seem reasonable to expect that the ion is also focussed if the polarity of DV and CV are reversed, for instance DV of –2500 volts and CV of +11 volts. This, however, is not observed and in fact the reversal of polarity in this manner creates a mirror image effect of the ion-focussing behavior of FAIMS. The result of such polarity reversal is that the ions are not focussed, but rather are extremely rapidly rejected from the device. The mirror image of a focussing valley is a hill-shaped potential surface. The ions slide to the center of the bottom of a focussing potential valley (2 or 3-dimensions), but slide off of the top of a hill-shaped surface, and hit the wall of an electrode. This is the reason for the existence, in the cylindrical geometry FAIMS, of the independent "modes" called 1 and 2. Such a FAIMS instrument is operated in one of four possible modes: P1, P2, N1, and N2. The "P" and "N" describe the ion polarity, positive (P) and negative (N). The waveform with positive DV, where DV describes the peak voltage of the high voltage portion of the asymmetric waveform, yields spectra of type P1 and N2, whereas the reversed polarity negative DV, waveform yields P2 and N1. The discussion thus far has considered positive ions but, in general, the same principles apply to negative ions equally.

A further improvement to the cylindrical FAIMS design is realized by providing a curved surface terminus of the inner electrode. The curved surface terminus is continuous with the cylindrical shape of the inner electrode and is aligned co-axially with an ion-outlet orifice of the FAIMS analyzer region. The application of an asymmetric waveform to the inner electrode results in the normal ion-focussing behavior described above, except that the ion-focussing action extends around the generally spherically shaped terminus of the inner electrode. This means that the selectively transmitted ions cannot escape from the region around the terminus of the inner electrode. This only occurs if the voltages applied to the inner electrode are the appropriate combination of CV and DV as described in the discussion above relating to 2-dimensional focussing. If the CV and DV are suitable for the focussing of an ion in the FAIMS analyzer region, and the physical geometry of the inner surface of the outer electrode does not disturb this balance, the ions will collect within a three-dimensional region of space near the terminus. Several contradictory forces are acting on the ions in this region near the terminus of the inner electrode. The force of the carrier gas flow tends to influence the ion cloud to travel towards the ion-outlet orifice, which advantageously also prevents the trapped ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focussing effect of the electric fields of the FAIMS mechanism. This is an example of a three-dimensional atmospheric pressure ion trap, as disclosed in U.S. Pat. No. 6,621,077, issued Sep. 16, 2003, in the name of Guevremont et al., the contents of which are herein incorporated by reference.

Ion focusing and ion trapping requires electric fields that are other than constant in space, normally occurring in a geometrical configuration of FAIMS in which the electrodes are curved, and/or are not parallel to each other. For example, a non-constant in space electric field is created using electrodes that are cylinders or a part thereof; electrodes that are spheres or a part thereof; electrodes that are elliptical spheres or a part thereof; and, electrodes that are conical or a part thereof. Optionally, various combinations of these electrode shapes are used.

As discussed above, one previous limitation of the cylindrical FAIMS technology is that the identity of the peaks appearing in the CV spectra are not unambiguously confirmed due to the unpredictable changes in $K_h$ at high electric field strengths. Thus, one way to extend the capability of instruments based on the FAIMS concept is to provide a way to determine the make-up of the CV spectra more accurately, such as by introducing ions from the FAIMS device into a mass spectrometer for mass-to-charge (m/z) analysis. Advantageously, the ion focusing property of cylindrical FAIMS devices acts to enhance the efficiency for transporting ions from the analyzer region of a FAIMS device into an external sampling orifice, for instance an inlet of a mass spectrometer. This improved efficiency of transporting ions into the inlet of the mass spectrometer is optionally maximized by using a 3-dimensional trapping version of FAIMS operated in nearly trapping conditions. Under near-trapping conditions, the ions that have accumulated in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a small orifice leading into the vacuum system of a mass spectrometer.

Additionally, the resolution of a FAIMS device is defined in terms of the extent to which ions having similar mobility properties as a function of electric field strength are separated under a set of predetermined operating conditions. Thus, a high-resolution FAIMS device transmits selectively a relatively small range of different ion species having similar mobility properties, whereas a low-resolution FAIMS device transmits selectively a relatively large range of different ion species having similar mobility properties. The resolution of FAIMS in a cylindrical geometry FAIMS is compromised relative to the resolution in a parallel plate geometry FAIMS because the cylindrical geometry FAIMS has the capability of focusing ions. This focusing action means that ions of a wider range of mobility characteristics are simultaneously focused in the analyzer region of the cylindrical geometry FAIMS. A cylindrical geometry FAIMS with narrow electrodes has the strongest focusing action, but the lowest resolution for separation of ions. As the radii of curvature are increased, the focusing action becomes weaker, and the ability of FAIMS to simultaneously focus ions of similar high-field mobility characteristics is similarly decreased. This means that the resolution of FAIMS increases as the radii of the electrodes are increased, with parallel plate geometry FAIMS having the maximum attainable resolution.

Note that, while the above discussion refers to the ions as being "captured" or "trapped", in fact, the ions are subject to continuous 'diffusion'. Diffusion always acts contrary to focussing and trapping. The ions always require an electrical, or gas flow force to reverse the process of diffusion. Thus, although the ions are focused into an imaginary cylindrical zone in space with almost zero thickness, or within a 3-dimensional ion trap, in reality it is well known that the ions are actually dispersed in the vicinity of this idealized zone in space because of diffusion. This is important, and should be recognized as a global feature superimposed upon all of the ion motions discussed in this disclosure. This means that, for example, a 3-dimensional ion trap actually has real spatial width, and ions continuously leak from the 3-dimensional ion trap, for several physical, and chemical reasons. Of course, the ions occupy a smaller physical region of space if the trapping potential well is deeper.

It is a limitation of the prior art FAIMS devices operating in a trapping or near trapping mode that the ions are difficult to extract from the FAIMS analyzer once they have been separated. Typically, the flow of carrier gas is used to prevent the ions from being attracted to one of the electrodes, and further to carry ions entrained therein out of the trapping region for detection. Of course, the flow of carrier gas is optimized for separation of ions during the time that they are resident within the analyzer region, and not for extracting the ions subsequent to their separation. In some cases, therefore, it is possible that the carrier gas flow rate will be other than sufficient to extract the selectively transmitted ions from the focusing region near the ion outlet. It would be advantageous to provide a method and a system for increasing the efficiency of ion extraction from the FAIMS analyzer by diverting the ion flow substantially away from the focusing region.

OBJECT OF THE INVENTION

In order to overcome these and other limitations of the prior art, it is an object of the present invention to provide a high field ion mobility spectrometer for separating ions in which trajectories of ions are affected by an ion diverter for directing the ions in a known fashion.

SUMMARY OF THE INVENTION

In accordance with the invention there is provided an apparatus for separating ions, comprising: a high field asymmetric waveform ion mobility spectrometer including:

two electrodes at least one of which is for receiving an asymmetric waveform electrical signal and for producing a field between the electrodes;

an ion inlet;

an analyzer region in communication with the ion inlet and defined by at least a first ion flow path between the two electrodes; and, an ion diverter separate from the two electrodes for diverting the ions from the ion flow path in a known fashion.

In accordance with the invention there is provided a method for separating ions, comprising the steps of:

a) providing an asymmetric waveform and a direct-current compensation voltage to an electrode to form an electric field, the field for effecting a difference in net displacement between ions in a time of one cycle of the applied asymmetric waveform for effecting a first separation of the ions by forming a subset thereof;

b) producing ions within an ionization source;

c) transporting said produced ions through the electric field along at least a first ion flow path in a direction approximately transverse to the electric field; and, d) diverting the selectively transmitted ions relative to the ion flow path absent the step of diverting in a predetermined fashion after separation.

BRIEF DESCRIPTION OF THE DRAWINGS

FIG. 5 shows a simplified block diagram of a modified analyzer region of an improved FAIMS device with at least an ion diverting device according to a fourth embodiment of the present invention;

FIG. 6 shows a simplified block diagram of another modified analyzer region of an improved FAIMS device with at least an ion diverting device according to a fifth embodiment of the present invention;

DETAILED DESCRIPTION OF THE INVENTION

Figure 1:
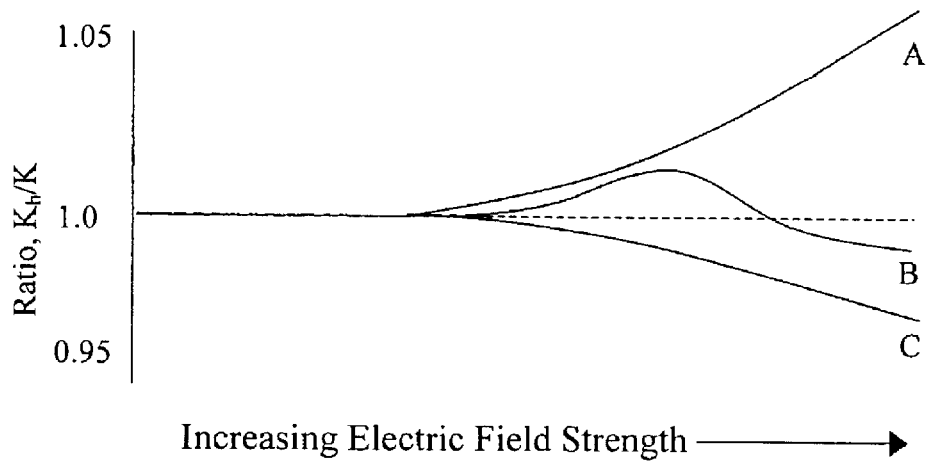
FIG. 1 shows three possible examples of changes in ion mobility as a function of the strength of an electric field.

Referring to FIG. 1, shown are three possible examples of the change in ion mobility properties with increasing electric field strength, as was discussed previously. The separation of ions in FAIMS is based upon a difference in these mobility properties for a first ion relative to a second ion. For instance, a first type A ion having a low field mobility $K_{1,low}$ is other than separated in a FAIMS device from a second type A ion having a second different low field mobility $K_{2,low}$, if under the influence of high electric field strength, the ratio $K_{1,high}/K_{1,low}$ is equal to the ratio $K_{2,high}/K_{2,low}$. Interestingly, however, this same separation is achieved using conventional ion mobility spectrometry, which is based on a difference in ion mobilities at low applied electric field strength.

Figure 2A:
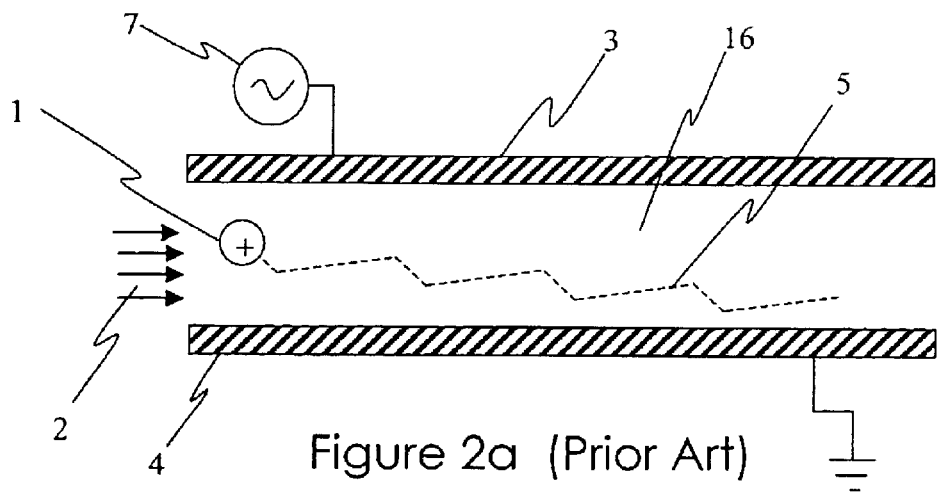
FIG. 2a illustrates the trajectory of an ion between two parallel plate electrodes under the influence of the electrical potential V(t)
Figure 2B:
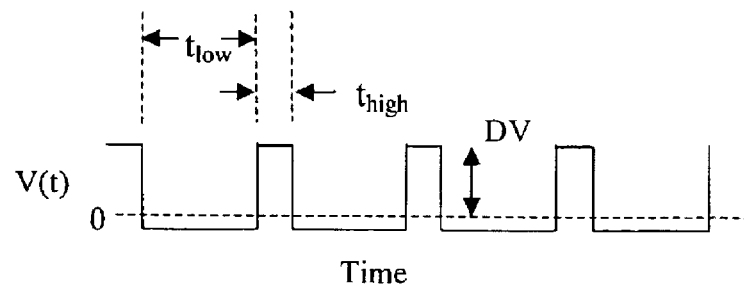
FIG. 2b shows an asymmetric waveform described by V(t)

Referring to FIG. 2a, shown is a schematic diagram illustrating the mechanism of ion separation according to the FAIMS principle. An ion 1, for instance a positively charged type A ion, is carried by a gas stream 2 flowing between two spaced apart parallel plate electrodes 3 and 4. One of the plates 4 is maintained at ground potential, while the other plate 3 has an asymmetric waveform described by V(t), applied to it. The peak voltage applied during the waveform is called the dispersion voltage (DV), as is shown in FIG. 2b. Referring still to FIG. 2b, the waveform is synthesized so that the electric fields during the two periods of time $t_{high}$ and $t_{low}$ are not equal. If $K_h$ and K are identical at high and low fields, the ion 1 is returned to its original position at the end of one cycle of the waveform. However, under conditions of sufficiently high electric fields, $K_h$ is greater than K and the distances traveled during thigh and $t_{low}$ are no longer identical. Within an analyzer region defined by a space 16 between the first and second spaced apart electrode plates, 3 and 4, respectively, the ion 1 experiences a net displacement from its original position relative to the plates 3 and 4 as illustrated by the dashed line 5 in FIG. 2a.

If a type A ion is migrating away from the upper plate 3, a constant negative dc compensation voltage CV is applied to plate 3 to reverse or "compensate" for this offset drift. Thus, the ion 1 does not travel toward either plate. If two species of ions respond differently to the applied high electric field, for instance the ratios of $K_h$ to K are not identical, the compensation voltages necessary to prevent their drift toward either plate are similarly different. To analyze a mixture of ions, the compensation voltage is, for example, scanned to transmit each of the components of a mixture in turn. This produces a compensation voltage spectrum, or CV spectrum.

Figure 3:
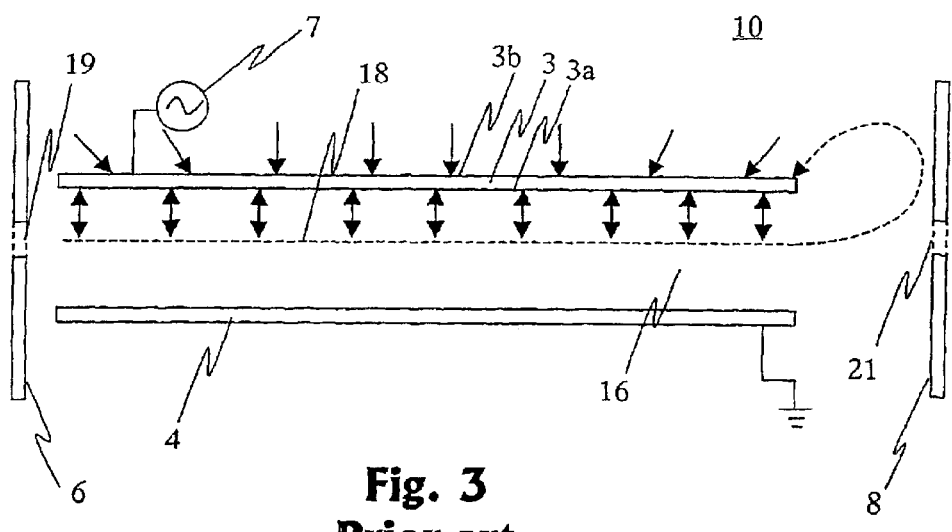
FIG. 3 shows a simplified block diagram of an analyzer region of a parallel plate FAIMS device according to the prior art.

Referring to FIG. 3, a simplified block diagram of a parallel plate FAIMS device according to the prior art is shown generally at 10. The analyzer region is defined by a space 16 between two flat, parallel plate electrodes 3 and 4, and between an ion-inlet electrode 6 having an ion-inlet orifice 19 and an ion-outlet electrode 8 having an ion-outlet orifice 21. The electrodes 3 and 4 are connected to an electrical controller 7 such that, in use, an asymmetric waveform and a superimposed dc compensation voltage is applied to electrode 3. Typically, the electrode 4 is maintained at a same dc voltage relative to each of the ion-inlet electrode 6 and the ion-outlet electrode 8. In this example, the asymmetric waveform and CV are set so that a particular species of positively charged ion (not shown) is transmitted through the analyzer region within space 16 between the plates 3 and 4, for instance the CV is negative, and the waveform has positive polarity. The "net" ion trajectory through the analyzer region is indicated in FIG. 3 by dotted line 18. In general, the powered electrode 3 is attracting the positive ion toward itself due to the negative dc bias, as indicated in FIG. 3 by the arrowheads of the electric force lines that are directed toward electrode 3. Fortunately, within the analyzer region 16 the effect of the asymmetric waveform is to push the ion away from the electrode 3, as is indicated in FIG. 3 by the arrowheads of the electric force lines that are directed away from electrode 3. As long as the electric fields are strong, and as long as the fields stay constant in strength, a balanced condition that is necessary to allow the ion to pass through the analyzer region 16 is maintained. This balanced condition is shown schematically in FIG. 3 as a series of double-headed electric force lines, comprising a DV and CV component, which are selected for transmitting ions having specific high field mobility properties.

Of course, the fields are not strong everywhere around the powered electrode 3. On a side 3a of the powered electrode 3 that opposes the second electrode 4, and on the end edges of the electrode facing one of the ion-inlet electrode 6 and the ion-outlet electrode 8, the fields are strong and the balanced condition exists. However, where the electric field strength changes, such as occurs on a side 3b of the powered electrode 3 at the end edges of the electrode facing one of the ion-inlet electrode 6 and the ion-outlet electrode 8, the ion path change rapidly, resulting in a dramatic redirection of the ion stream. This redirection lacks the balanced conditions that the ion stream experiences between the plates 3 and 4. This means that on the back side 3b of the powered electrode 3 the ion will impact onto the metal surface, pulled by the negative polarity of the applied CV. Although the ion maintains a stable trajectory along side 3a where the opposing electrical forces are balanced, upon exiting space 16 the ion follows a curved path towards the back side 3b of electrode 3. The negative dc bias applied to electrode 3 creates a potential hillside for the ion to slide down. The carrier gas flow is other than able to prevent this downward slide unless the CV is very low or the gas flow is very high. Even if impact with the plate 3 is avoided, many ion paths do not proceed toward the ion-outlet orifice 21 of the device 10, the ions being lost to a collision with a different part of the FAIMS apparatus.

Figure 4A:
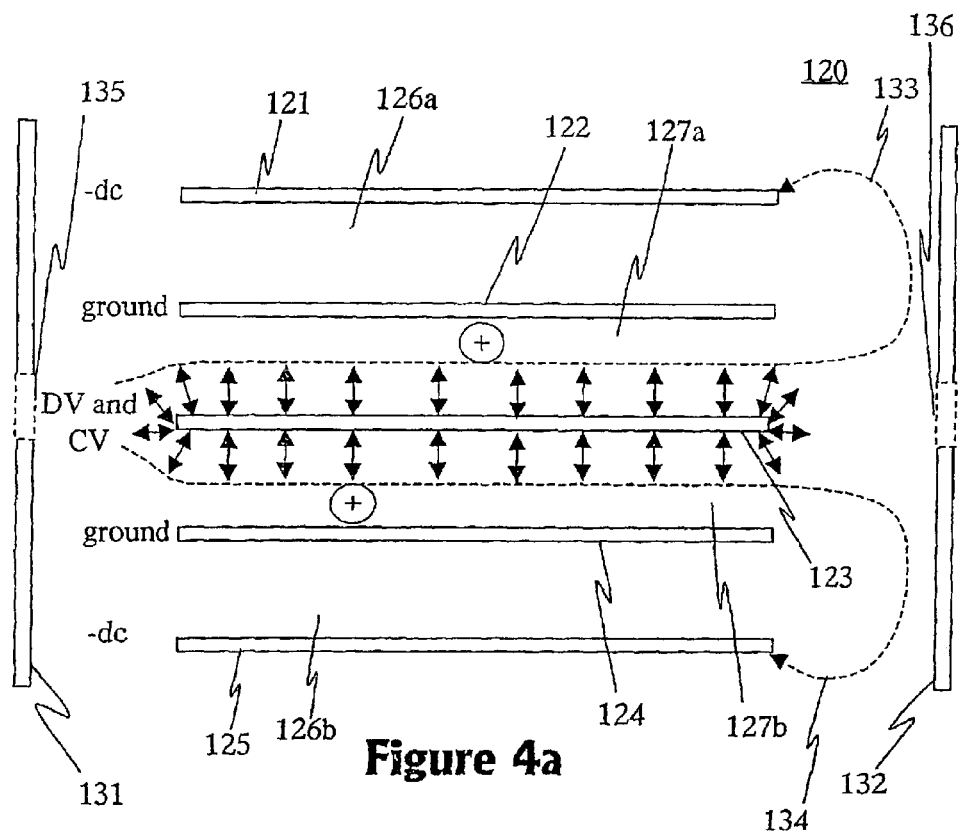
FIG. 4a shows a simplified block diagram of an analyzer region of an improved FAIMS device with at least an ion diverting device, as operating in a first mode, according to a first embodiment of the present invention.
Figure 4B:
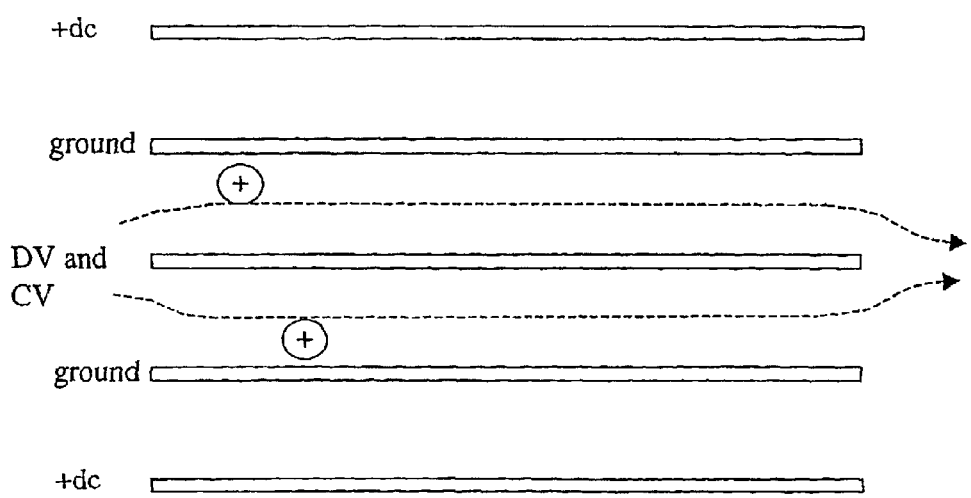
FIG. 4b shows a simplified block diagram of an analyzer region of an improved FAIMS device with at least an ion diverting device, as operating in a second mode, according to a first embodiment of the present invention.

Referring to FIGS. 4a and 4b, a first preferred embodiment of the present invention is shown generally at 120. Additionally, FIGS. 4c to 4f show different modes of operation of a same electrode geometry as shown FIG. 4a, wherein different combinations of applied voltages are described. Therefore, reference numerals indicating elements of the drawings identical to those elements previously described with reference to FIG. 4a have been omitted from FIGS. 4b to 4f in the interest of clarity and brevity. Of course, an ion-inlet electrode 131 and an ion-outlet electrode 132, described with reference to FIG. 4a below, have similarly been omitted from FIGS. 4b to 4f, but are understood to have a crucial role in producing the strong electric fields that are described subsequently for each mode of operation with reference to FIGS. 4b to 4f. Further, ions are shown schematically in FIGS. 4a to 4f (not to scale) as circles in which a '+' sign appears to indicate ion species of positive polarity charge, and as circles in which a '−' sign appears to indicate ion species of negative polarity charge. Circles having a dark border are used in some cases, for instance to distinguish between two ions having a same charge but having different mobility properties as a function of electric field strength.

Referring again to FIG. 4a, the analyzer region includes a first electrode 121, a second electrode 122, a third electrode 123, a fourth electrode 124 and a fifth electrode 125 in a substantially uniformly spaced-apart stacked arrangement. Thus, two spaces 126a and 127a are disposed on a first side of electrode 123 and two different spaces 126b and 127b are disposed on the opposite side of electrode 123. In a most basic version of the present embodiment, the electrodes shown in FIG. 4a are flat parallel plates with square ends. In a first mode of operation a CV and DV is applied to the third electrode 123, while the second electrode 122 and the fourth electrode 124 are maintained at ground potential or some other dc potential. In this case, ions are drawn to the third electrode 123 due to the dc bias, and are carried by the uniform gas flow predominantly through spaces 127a and 127b. Since the electrodes are flat parallel plates the electric fields within each space 127a and 127b are constant, such that ion focusing does not occur. Additionally the electric fields are the same within each space, such that a same ion is selectively transmitted through both spaces 127a and 127b. Of course, the electrodes are mounted in an insulating support, which is omitted for clarity in FIG. 4a. Each space 126a, 127a, 127b and 126b defines a separate ion flow path that is closed on four sides such that it is other than possible for ions to move from one space to the other space. Further, a physical barrier (not shown) is provided along the outer surfaces of electrodes 121 and 125 for preventing the flow of carrier gases through spaces other than 126a, 127a, 127b and 126b.

Typically, electrode 123 is connected to an electrical controller (not shown) such that, in use, an asymmetric waveform and a superimposed first dc voltage, wherein the superimposed first dc voltage is other than the compensation voltage, is applied to the electrode 123. The electrodes 122 and 124 are connected to at an electrical controller (not shown), such that, in use, electrodes 122 and 124 are maintained at a predetermined second dc voltage or at a ground potential. The ion-inlet electrode 131, having an ion-inlet orifice 135 therethrough, and an ion-outlet electrode 132, having an ion-outlet orifice 136 therethrough, are also maintained at predetermined dc voltages by power supplies (not shown). The CV is the difference between the superimposed first dc voltage applied to the electrode 123 and the second dc voltage applied to the electrodes 122 and 124. Those ions having appropriate mobility properties for a particular combination of DV and CV are selectively transmitted through the analyzer region, for instance within space 127a between the electrodes 122 and 123, and within space 127b between the electrodes 123 and 124. For example, the selective transmission of an analyte ion through the FAIMS analyzer region may require the electrode 123 to be biased 5 volts lower than electrodes 122 and 124, for instance the CV is negative 5 volts, and for the waveform to be of positive polarity, for example 2500 volts. The electrodes 121 and 125 are connected to at least a dc voltage controller, for instance two separate dc voltage controllers (not shown), such that, in use, electrodes 121 and 125 are maintained at a third predetermined dc voltage or at ground potential.

A 'net' trajectory for a selectively transmitted ion through the FAIMS analyzer region is shown diagrammatically in FIG. 4a at dotted lines 133 and 134. In general, the powered electrode 123 is attracting the ions toward itself due to the negative dc bias relative to electrodes 122 and 124, as indicated in FIG. 4a by the arrowheads of the electric force lines that are directed toward electrode 123. Fortunately, within the FAIMS analyzer region the effect of the asymmetric waveform is to push the ion away from the electrode 123, as is indicated in FIG. 4a by the arrowheads of the electric force lines that are directed away from electrode 123. As long as the electric fields are strong, and as long as the fields stay constant in strength, a balanced condition that is necessary to allow the ion to pass through the analyzer region is maintained. This balanced condition is shown schematically in FIG. 4a as a series of double-headed electric force lines, comprising a DV and CV component that are selected for transmitting ions having specific high-field mobility properties. This balanced condition extends completely around the inlet end of the electrode 123 facing the ion-inlet electrode 131 and completely around the outlet end of the electrode 123 facing the ion-outlet electrode 132.

Unlike the prior art parallel plate FAIMS, the electric fields extend on both sides of the third electrode 123 symmetrically within the analyzer region, such that the ion continues to "see" the same balancing electric forces and will continue along a stable trajectory to exit the analyzer. The electrical forces for selectively transmitting the ion remain balanced beyond the physical limit of the electrodes because the two sides of the powered third electrode 123 are symmetrical. For instance a metal conductive surface of electrodes 122 and 124 is located a same distance from each surface of the powered third electrode 123. Under these conditions, even slowly flowing gas will tend to keep the ions positioned near the trailing edge of the electrode, in a position close to the ion-outlet electrode 132. Further, if the third electrode 123 of the system shown generally at 120 in FIG. 4a is narrow relative to the spaces 127a and 127b between the electrodes, then the specific shape of the corners at the edges of the electrode plates will other than critically influence the ion trajectory. For instance rounded or squared corners behave more or less the same in terms of the resulting fields that the ion will experience in this region. This is because the electric fields tend to 'smooth' themselves out over a distance away from a corner of the electrode, such that effectively the fields around the electrode look exactly the same as if it was rounded once you move more than some distance away. If the electrode is thick, for example more than approximately 20% of the thickness of the spaces, then the shape is important. Also, if the ion trajectory is very close to the third electrode 123, a contour at an edge of the electrode has more influence on the path of travel than when the ions are further away from the third electrode 123.

Advantageously, when these balanced condition extend around the inlet edge of the electrode 123, collisions between the ions entering through the ion-inlet orifice 135 in the ion-inlet electrode 131 and the leading edge of electrode 123 are minimized. The ions are prevented from approaching the electrode 123 by the effective repelling force that is created by the asymmetric waveform. Similarly, at the opposite end of the electrode 123 the balanced condition tends to pull the ions towards the electrode 123 as they pass by the outlet end of the electrode 123, giving the 'near-trapping' conditions shown by the ion trajectory shown at dotted lines 133 and 134 in FIG. 4b. The ions would otherwise be trapped at the outlet edge of electrode 123, for example the ions are unable to move in any direction, absent a gas flow that is sufficiently strong to carry the ions to the ion-exit orifice. Of course, the dc voltage applied to the ion-exit electrode 132 is adjusted to help pull the ions away from the trailing edge of electrode 123 in a controlled fashion. Alternatively, the ions are detected by electrometric means (not shown) external to the analyzer region. As previously described, electrodes 121 and 125 are connected to at least a dc controller, such that a dc bias is optionally applied to the first and fifth electrodes 121 and 125 for diverting the ions. For instance in FIG. 4a positively charged ions are selectively transmitted through spaces 127a and 127b and collected at electrodes 121 and 125, which have a negative dc bias applied. Alternatively, a positive dc bias is applied to electrodes 121 and 125 for focusing the positively charged ions into a narrow beam exiting the analyzer region for highly efficient extraction, as shown for a second mode of operation in FIG. 4b. Of course in FIG. 4b, the ion-outlet electrode 123 is additionally provided with an orifice for transmitting ions to a detector.

Figure 4C:
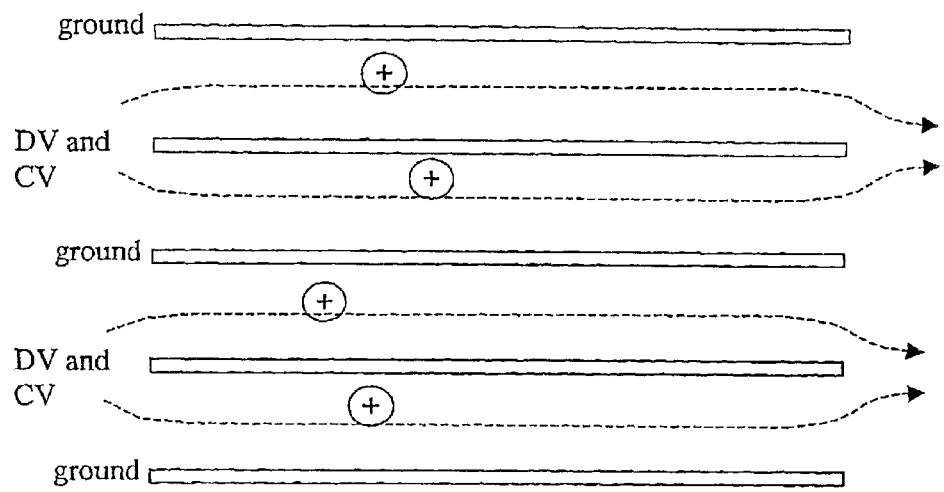
FIG. 4c shows a simplified block diagram of an analyzer region of an improved FAIMS device with at least an ion diverting device, as operating in a first mode, according to a second embodiment of the present invention.
Figure 4D:
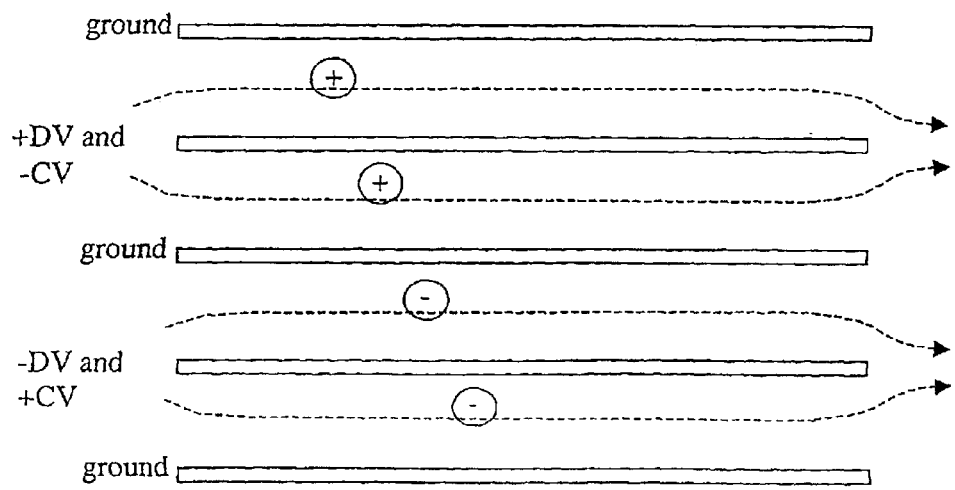
FIG. 4d shows a simplified block diagram of an analyzer region of an improved FAIMS device with at least an ion diverting device, as operating in a second mode, according to a second embodiment of the present invention.

In a second preferred embodiment of the present invention, a same combination of CV and DV are applied to the second electrode 122, and to the fourth electrode 124 while the first electrode 121, the third electrode 123 and the fifth electrode 125 are maintained at ground potential as shown at FIGS. 4c and 4d. Alternatively the first, third and fifth electrodes are maintained at some other dc potential. In this mode the constant electric fields within the spaces 126a, 127a, 127b and 126b are identical, such that a same ion species is selectively transmitted through each of the four spaces. Advantageously, the ions will be distributed along four analyzer regions instead of only two, which reduces the space-charge induced ion-ion repulsion and minimizes ion losses in the analyzer region. Ion focusing occurs at the outlet edge of each powered electrode 122 and 124, as was previously discussed with reference to FIG. 4b.

In an alternate mode of operation for the second preferred embodiment, a different combination of CV and DV are applied to the second electrode 122, and to the fourth electrode 124 while the first electrode 121, the third electrode 123 and the fifth electrode 125 are maintained at ground potential as shown in FIG. 4d. Alternatively the first, third and fifth electrodes are maintained at some other dc potential. FIG. 4d illustrates a mode of operation wherein a positive polarity waveform and negative CV are applied to the second electrode 122, whereas a negative polarity waveform and positive CV are applied to the fourth electrode 124. As shown in FIG. 4d, positive ions are selectively transmitted through spaces 126a and 127a, whereas negative ions are selectively transmitted through spaces 127b and 126b. This is referred to as a multi-mode parallel plate FAIMS. The current mode of operation selectively transmits a same species of positive ion within spaces 126a and 127a, since the electric fields are identical within the spaces 126a and 127a. Similarly, a same species of negative ion is transmitted within spaces 126b and 127b, since the electric fields are identical within the spaces 126b and 127b.

Figure 4E:
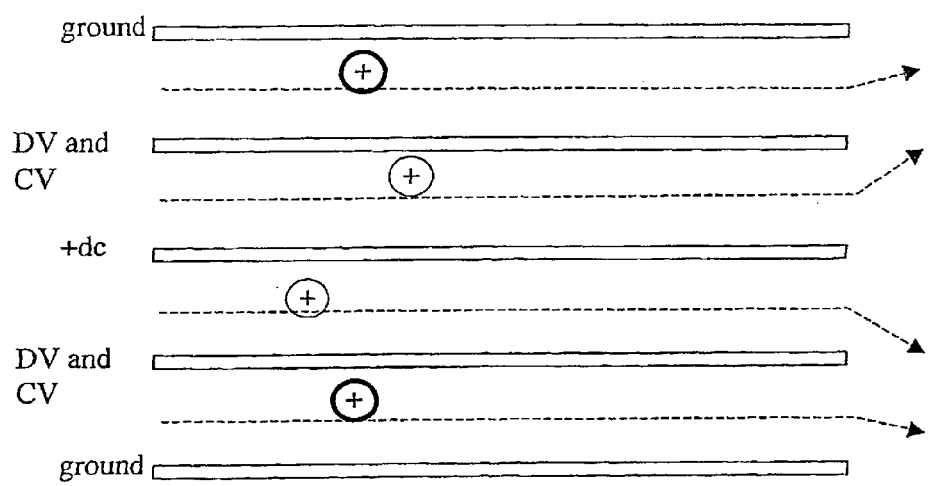
FIG. 4e shows a simplified block diagram of an analyzer region of an improved FAIMS device with at least an ion diverting device, as operating in a first mode, according to a third embodiment of the present invention.
Figure 4F:
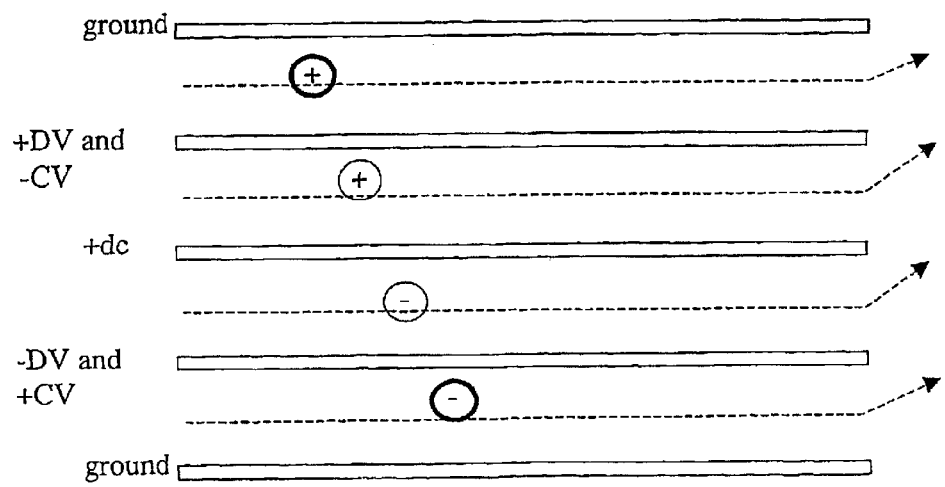
FIG. 4f shows a simplified block diagram of an analyzer region of an improved FAIMS device with at least an ion diverting device; as operating in a second mode, according to a third embodiment of the present invention.

As shown in FIGS. 4e and 4f for a third embodiment of the present invention, when the third electrode 123 is electrically insulated from the remaining electrodes, a dc potential is optionally applied to the third electrode 123 for diverting the ions in a predetermined manner. In FIG. 4e an example is shown wherein a same DV and CV combination are applied to the second and fourth electrodes 122 and 124 for selectively transmitting a same positive ion species. Then, a positive dc potential applied to the ion diverter third electrode 123 will cause all ion trajectories to diverge away from the central axis of the device. Alternatively, a negative dc potential applied to the ion diverter third electrode 123 will cause all ion trajectories to diverge towards the central axis of the device, for instance the positive ions will be focused into a narrow beam coaxial with the center axis of the device. If a more negative dc potential is applied, then the positive ions are optionally collected and detected at the third electrode 123. Of course, the electric fields within spaces 126a and 127a are different, because on one side of the powered electrode 122 the compensation voltage is determined relative to a ground potential, whereas on the opposing side the compensation voltage is determined relative to a predetermined applied dc potential. Consequently, positive ions are transmitted through each space, however, a first species of positive ion is transmitted through spaces 126a and 126b, and a second different species of positive ion is transmitted through spaces 127a and 127b.

In FIG. 4f an alternative mode of operation of the third embodiment is shown, wherein a different DV and CV combination is applied separately to the second and fourth electrodes 122 and 124. For instance, a positive polarity waveform and negative CV are applied to the second electrode 122, whereas a negative polarity waveform and positive CV are applied to the fourth electrode 124. As shown in FIG. 4f, positive ions are selectively transmitted through spaces 126a and 127a, whereas negative ions are selectively transmitted through spaces 127b and 126b. Operated in the mode illustrated in FIG. 4f, the FAIMS analyzer functions as a four-mode FAIMS device, characterized in that a first species of positive ion is transmitted through space 126a, a second different species of positive ion is transmitted through space 127a, a first species of negative ion is transmitted through space 127b, and a second different species of negative ion is transmitted through space 126b. Of course, in practice it is difficult to control conditions appropriate for the selective transmission of four different ion species, nevertheless it is possible in principle to selectively transmit one to four ion species in parallel using the third embodiment of the present invention.

Still referring to FIG. 4f, a positive dc potential applied to the ion diverter third electrode 123 causes the positive ions that are selectively transmitted through spaces 126a and 127a to diverge away from the third electrode 123 of the device, whereas the negative ions that are selectively transmitted through spaces 127b and 126b will see an attractive force and be diverted towards the third electrode 123 of the device. Alternatively, a negative dc potential applied to the ion diverter third electrode 123 causes the positive ions that are selectively transmitted through spaces 126a and 127a to diverge towards the third electrode 123 of the device, whereas the negative ions that are selectively transmitted through spaces 127b and 126b will see an repulsive force and be diverted away from the third electrode 123 of the device. Of course, by applying a more positive dc bias toward electrode 123 it is possible to collect negative ions at electrode 123, with the positive ions being diverted more strongly. Conversely, by applying a more negative dc bias toward electrode 123 it is possible to collect positive ions at electrode 123, with the negative ions being diverted more strongly.

Although the preferred embodiment of the present invention as described with reference to FIGS. 4c to 4f includes an electrode 123 for diverting ions, optionally other ion diverting means are used. For example, a slit-shaped orifice including a gas jet is optionally provided in place of electrode 123 for providing a flow of gas for diverting the ions. The ion diverting gas flow augments the uniform gas flow that, in use, is moving through the analyzer region for carrying the ions in a direction transverse to the applied electric fields. Advantageously, the ion diverting gas flow is used to push ions from the analyzer region through an outlet for subsequent analysis or collection. Further advantageously, the ion diverting gas flow diverts positively charged ions and negatively charged ions in a same direction, either away from the ion diverting means or towards the ion diverting means.

The embodiments described with reference to FIGS. 4a to 4f have employed flat parallel plate electrodes with square end edges. Optionally, the first to fifth electrode plates 121 to 125, respectively, are parallel flat-plate electrodes having a leading and a trailing edge, with respect to a direction of ion flow through the analyzer region when in use, that are rounded in cross section. The radius of curvature of the smooth curve provided at the leading and trailing edges of each electrode 121 to 125 are appropriate to focus and trap the ions at leading and trailing edges, and of course the electrode plates are thick enough to accommodate the radius of curvature. Of course, in the case where each of the first through fifth electrodes 121 to 125 are provided with leading and trailing edges that are rounded in cross sections, ion focusing will occur only at those electrodes to which a DV and superimposed CV are applied. This focussing effect with flat-plate electrodes is disclosed in co-pending U.S. patent application Ser. No. 10/221,480 in the name of R. Guevremont and R. Purves.

Optionally, in addition to providing a curved cross section at the leading and trailing edges of the electrode plates, at least one of the leading edge and the trailing edge are further shaped with a concave smooth curve that is directed away from the direction of ion flow. The concave smooth curve at the at least an edge of the electrode plates is for producing electric fields that are shaped to direct the flow of ions generally inwardly towards the center of the electrode plate. Advantageously the ions are focused into a narrow beam before entering the flat plate analyzer region, which minimizes ion losses during separation. Further advantageously, the efficiency of ion extraction is improved at the trailing edge of the plate by focusing the ions further into a narrow beam prior to their extraction, thus maximizing ion transmission and minimizing overall losses.

Further optionally the first through fifth electrode plates 121, 122, 123, 124 and 125 are curved, wherein the first through fifth curved electrode plates are referred to as 151, 152, 153, 154 and 155, respectively, for a fourth embodiment of the present invention as A shown in FIG. 5a. The series of electrode plates 121, 122, 123, 124 and 125 are mounted into an insulating support 64, which has grooves to hold the plates at fixed distances of separation between the plates. An ion-inlet electrode (not shown) and an ion-outlet electrode (not shown) are additionally provided at the ion-inlet and the ion-outlet edges, respectively, of the electrode plates 151, 152, 153, 154 and 155. The ion-inlet electrode and the ion-outlet electrode having an ion-inlet orifice and an ion-outlet orifice, respectively, each orifice being aligned with electrode plate 153. The ion-inlet electrode and the ion-outlet electrode play a crucial role in producing the high strength electric fields near the ion-inlet and ion-outlet edges, respectively, of the curved electrode plates.

Of course, such a curved electrode geometry produces non-constant electric fields, such that in the fourth embodiment of the present invention a focusing region exists within each space 156a, 157a, 157b and 156b. Further, the field produced on one side of a powered electrode plate is other than identical to the field that is produced on the opposite side of the powered electrode plate. Interestingly, for the mode of operation described with reference to FIG. 4a or 4b in which the parallel plate electrodes are replaced by curved electrode plates, two different species of ions are typically transmitted; a first ion species within space 157a and a second ion species within space 157b. Of course, for the mode of operation described with reference to FIG. 4d, 4e or 4f in which the electrodes are curved electrode plates, four different ion species are typically transmitted; a first ion species within space 156a, a second ion species within space 157a, a third ion species within space 157b, and a fourth ion species within space 156b. FIG. 5b shows the electrode plate 153 is optionally shaped with curved ends for directing ions generally inwardly toward the center of the electrode edge. Further optionally, each of the other electrode plates 151, 152, 154 and 155 are also shaped for directing the ion trajectories.

Referring to FIGS. 6a and 6b, a fifth embodiment of the present invention having a lens shaped third electrode 163 is described. Two curved electrodes 161, 162 are disposed on one side of the lens shaped third electrode 163, and two other curved electrodes 164, 165 are disposed on an opposite side of the lens shared third electrode 163. As discussed previously, curved electrode geometry produces non-constant electric fields, such that in the fifth embodiment of the present invention a focusing region exists within each space 166a, 167a, 167b and 166b. The series of electrodes 161, 162, 163, 164 and 165 are mounted into an insulating support 64, which has grooves to hold the electrodes at fixed distances of separation between the electrodes. When an appropriate combination of DV and CV is applied to the electrode 163, identical electric fields that are non-constant in space are produced within spaces 167a and 167b, such that one species of ion is selectively transmitted. Alternatively, a combination of DV and CV is applied to electrodes 162 and 164. If a same combination of DV and CV is applied to both electrodes 162 and 164, then identical non-constant electric fields are produced within spaces 166a and 166b, and different identical non-constant electric fields are produced in spaces 167a and 167b. In this example a first species of ion is selectively transmitted through spaces 166a and 166b, and a second different species of ion is selectively transmitted through spaces 167a and 167b. Alternatively, if a different combination of DV and CV, for example the polarities of each potential is reversed, then different, non-constant electrical fields are produced within each space 166a, 166b, 167a and 167b. In this example, a different species of ion is selectively transmitted through each different space, 166a, 166b, 167a and 167b. FIG. 6b shows the electrode plate 163 is optionally shaped with curved ends for maximizing ion transmission.

Referring again to FIGS. 4a to 4f, two-dimensional ion focusing does not occur within the spaces 126a, 127a, 127b and 126b when the electrodes 121, 122, 123, 124 and 125 are flat, parallel plate electrodes. Thus, while it is assumed that only one ion species is selectively transmitted for a given combination of DV and CV, in fact a subset of ions are transmitted, wherein each ion species of the subset of ions has an approximately same appropriate mobility properties. Of course, two-dimensional ion focusing does occur within the spaces 156a, 157a, 157b and 156b between the curved electrode plates 151, 152, 153, 154 and 155, shown in FIG. 5a. In this latter case, while a subset of ions having appropriate mobility properties are transmitted also, the two-dimensional ion focussing effect that exits between the curved electrode plates reduces significantly the range of appropriate mobility properties. Advantageously, a subset of ions including fewer different ion species are transmitted through an analyzer region between curved electrode plates, relative to the subset of ions that are transmitted through an analyzer region between flat, parallel plate electrodes.

Figure 7:
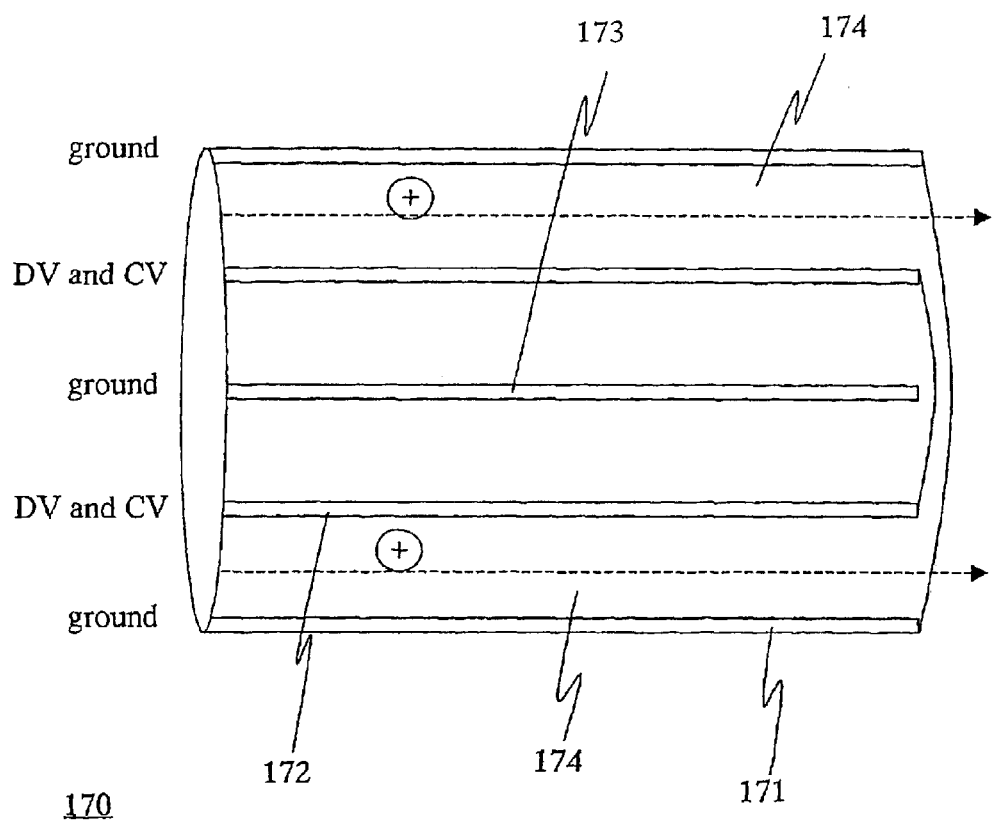
FIG. 7 shows a simplified block diagram of another cylindrical geometry FAIMS device with a ion diverting device according to a sixth embodiment of the present invention.

Of course, the analyzer regions according to the first, second and third embodiments of the present invention, as described with reference to FIGS. 4a to 4f, have a rotational axis of symmetry that is coaxial with the third electrode 123 and within the plane of the drawing. Rotation about this rotational axis of symmetry leads to a concentric cylinder FAIMS device, in which electrodes 121 and 125 form a continuous outer cylindrical surface 171, electrodes 122 and 124 form a continuous inner cylindrical surface 172 and electrode 123 forms an ion diverter 173 that is coaxially aligned with the outer and inner concentric cylinder electrodes 171 and 172, respectively. Of course, a single annular analyzer region 174 is defined by the space between the outer cylindrical electrode 171 and the inner cylindrical electrode 172. This is a sixth embodiment of the invention and will be described with reference to FIG. 7. The CV and DV are applied to the inner cylindrical electrode 172 in the example that is illustrated in FIG. 7; however, the CV and DV is alternatively applied to the outer cylindrical electrode 171. Since the same DV and CV must be applied to a cylindrical electrode, only one species of ion is transmitted through the analyzer region at one time. The ion diverter 173, in the form of a probe electrode, is shown at ground potential in FIG. 7, however in practice the probe electrode 173 is biased at negative or positive dc. In the case of positive ions being transmitted, a negative dc bias applied between the probe electrode 173 and the inner cylindrical electrode 172 will divert ions toward the probe electrode 173. If the negative dc bias is strong enough, ions will impact the probe electrode and are optionally detected. Alternatively, if a positive dc bias applied between the probe electrode 173 and the inner cylindrical electrode 172, the positively charged ions will be diverted away from the probe electrode 173. With an appropriate negative dc bias, ions will be focused into a narrow beam substantially axially aligned with the probe electrode for extraction from the analyzer region through an ion outlet.

Alternatively, the device shown generally at 170 in FIG. 7 has an ion diverter 173 in the form of an orifice having a gas nozzle for directing a jet of gas along the central axis of the inner electrode 172. The ion diverting gas jet pushes ions away from the terminus of the inner cylinder for extraction through an ion-outlet orifice (not shown) in an ion-outlet electrode (not shown).

Figure 8:
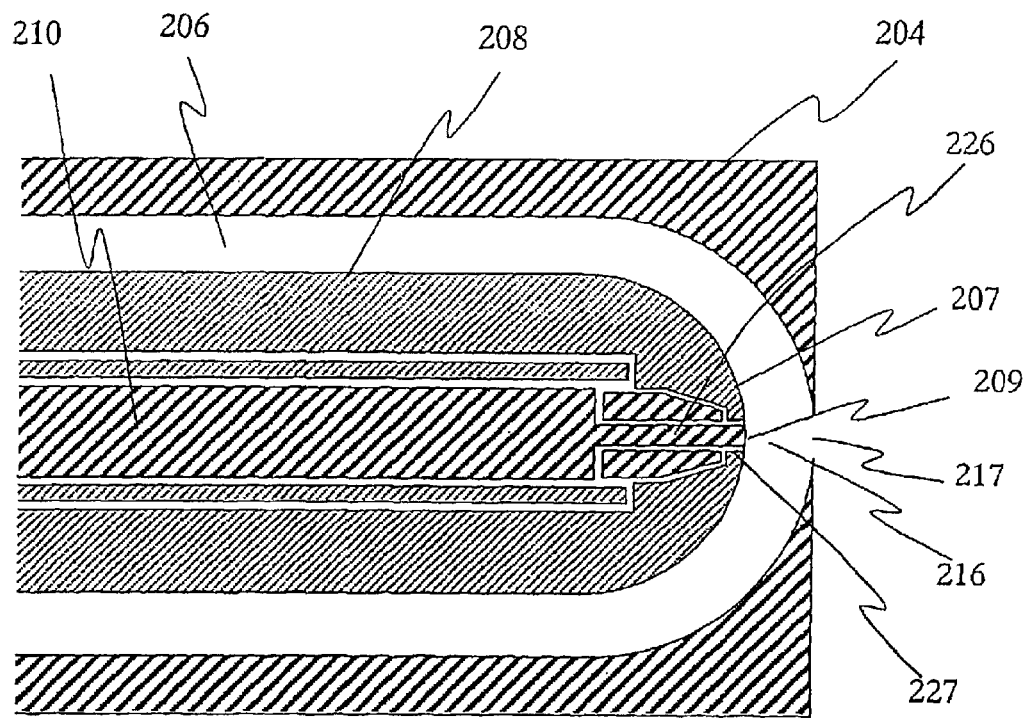
FIG. 8 shows a simplified block diagram of another cylindrical geometry FAIMS device with a ion diverting device according to a seventh embodiment of the present invention.

Referring to FIG. 8 shown is a simplified block diagram of a cylindrical geometry FAIMS device with an ion diverting device according to a seventh embodiment of the present invention. The seventh embodiment is very similar to the sixth embodiment, except the inner cylindrical electrode 208 is provided with a curved surface terminus 207, and the inner surface of the outer electrode 204 is shaped to maintain a substantially uniform distance to the inner cylindrical electrode 208 near the curved surface terminus 207. This geometry of FAIMS is referred to as a dome-FAIMS or dFAIMS. Shown also in FIG. 8 is an ion diverter 210 in the form of a probe electrode whose outer surface is continuous with the outer surface of the inner electrode 208 only at a small region 209 near the tip of the inner electrode. The ion diverter 210 is coaxially aligned with the inner cylindrical electrode 208 and the outer cylindrical electrode 204, and with an ion-outlet orifice 217 in the outer cylindrical electrode 204. It should be noted that the ion diverter 210 is easily removed from the FAIMS apparatus when so desired. Optionally, the ion diverter 210 is operated at a same voltage as the inner electrode 208, such that the electric fields near the terminus 207 are other than perturbed by the ion diverter 210.

The device called dFAIMS is typically used in two fashions of operation. First, it is used for 3-dimensional trapping, since the ions that are swept along the inner electrode 208 through space 206 arrive at the tip of the dome and are unable to proceed further because of the trapping action that extends along the sides of the inner electrode and around the tip of the electrode. This has been discussed in greater detail above with respect to FIG. 4a. Secondly, the device is optionally operated in continuous flow mode, if the electrode voltages are such that the stream of ions, which travel along the side of the inner electrode 208 through space 206, escape from the zone near the tip of the electrode. The ions tend to travel along the curved spherical surface of the inner electrode towards the central axis of the inner electrode 208, following the focusing fields, and are extracted as a narrow beam of ions.

The dFAIMS is improved by the addition of a probe electrode, the ion diverter 210 in FIG. 8, through the center of the inner electrode 208. The purpose of this electrode is to modify the electric fields near the terminus of the dome 207 of the inner electrode 208. The objectives are two-fold. First, the ions that accumulate near the terminus of 207 the inner electrode 208 are ejected or forced away from the inner electrode 208 by the repulsive forces of an electric field applied via a voltage on the probe electrode 210 relative to the inner electrode 208. Secondly, under some circumstances it is advantageous to pull the ions out of the trapping region towards this probe electrode 210. Ultimately the probe electrode 210 is used, for example, to collect a sample of the ions that collide with the surface of the probe electrode 210 that is exposed and substantially continuous with the inner electrode 208 at the tip of the domed surface 207 of the inner electrode 208.

The probe electrode 210 is supported and aligned by insulating materials, and extends to the surface 209, which is substantially continuous with the surface of the inner electrode 208. The asymmetric waveform that is applied to the inner electrode 208 through a connection screw (not shown) is also applied to the probe electrode 210. The probe electrode 210 does not contact the inner electrode 208, and a set of insulators (not shown) serve to suspend the probe electrode 210 away from the surfaces of the inner electrode 208. An additional electronic source (not shown) for applying a small dc bias between the probe electrode 210 and the inner electrode 208 is also provided.

Figure 9:
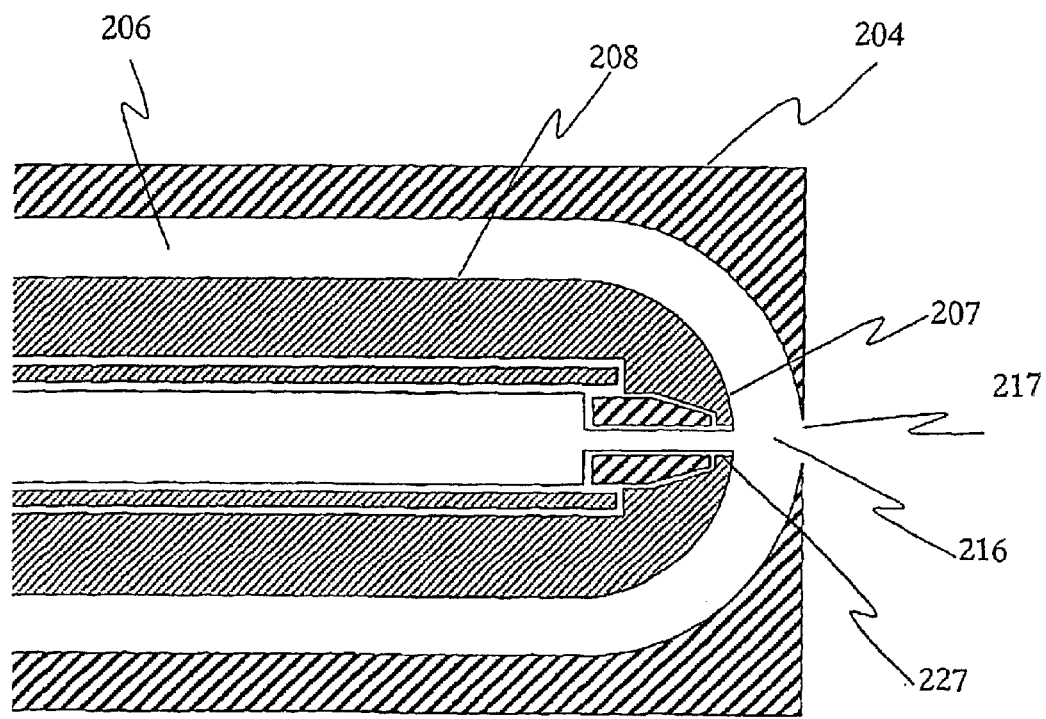
FIG. 9 shows a simplified block diagram of a cylindrical geometry FAIMS device with another ion diverting device according to a seventh embodiment of the present invention.

Still referring to FIG. 8 there is a small space between the short cylindrical rod 226 and the short cylindrical hole 227 drilled into the center of the inner electrode 208. Although this space is important for electrical insulation purposes, the space also serves as a conduit for an (optional) flow of gas. The gas flow serves several potential purposes. First, a gas flow traveling from the analyzer region into the channel between rod 226 and hole 227 serves to ensure that no contaminants are added to the analyzer region via this channel. If the gas flows into the channel, the flow will augment the existing flow along the analyzer region 206, and reduce the residence time of the ions inside the FAIMS, and bring the ions more quickly to the tip of the inner electrode 208. The dimensions of the conduit between rod 226 and 227 are optionally small or wide. The removal of rod 226, as shown in FIG. 9, to permit the hole 227 to be used only for the flow of gas is feasible with minimum modifications to this version of FAIMS.

A second optional use for the gas flow through the hole 227 is also envisioned. The ions that are trapped in the region 216 are optionally reacted chemically with a gas that exits from the hole 227 in the tip of the inner electrode 208. An example of a gas that reacts with an ion is carbon dioxide, which is known to form complexes with some types of ions. This new complex has different mobility properties compared to the bare ion, permitting that ion to leave the trapping region 216 for detection, even if another non-reactive ion resides in the trapping region 216. Similarly reactant gas is optionally used to reject some unwanted ion by forming a complex whose properties of mobility at low and high fields are no longer appropriate for the storage of this ion under the prevailing conditions of CV and DV, thereby increasing the relative number of the of ions of interest within the trapping region.

A third purpose for a gas flow out of the hole 227 in the inner electrode 208 is easily visualized. This gas flow is used to assist in ejecting ions out of the trapping region 216, if the flow along the analyzer region 206 is not sufficiently high for this purpose. The flow along the analyzer region 206 must in practice be set for the optimum separation of ions along the annular space between the outer electrode 204 and the inner electrode 208. This flow along the analyzer region 206 may not be the optimum flow necessary to move ions out of the dFAIMS at the tip of the inner electrode 208. A gas flow into or out of the hole 227 in the inner electrode 208 will serve to permit optimum flows both in the analyzer region 206 and out of the hole 217 in the outer electrode 204 which leads to an optional ion detection system (not shown).

Of course, numerous other embodiments could be envisioned, without departing significantly from the teachings of the present invention.

What is claimed is:

1. An apparatus for separating ions, comprising:
    a high field asymmetric waveform ion mobility spectrometer including:
        two electrodes at least one of which is for receiving an asymmetric waveform electrical signal and for producing a field between the two electrodes;
        an ion inlet;
        an analyzer region in communication with the ion inlet and defined by at least a first ion flow path through the field between the two electrodes and a second other ion flow path;
        an inlet for introducing a flow of a carrier gas into the analyzer region; and,
        an ion diverter electrode separate from the two electrodes, for receiving an electrical signal and for producing an electric field for diverting the ions from the at least a first ion flow path in a known fashion relative to an ion flow path that is expected absent the diverter electrode and for diverting the ions from the second other ion flow path in a known fashion relative to an ion flow path that is expected absent the diverter electrode, the diverter electrode disposed between the at least a first ion flow path and the second other ion flow path.

2. An apparatus according to claim 1, wherein the two electrodes are concentric coaxially aligned generally cylindrical inner and outer electrode bodies forming an annular space therebetween.

3. An apparatus according to claim 2, wherein the inner electrode is provided with a terminus shaped for directing ions generally radially inward toward the central axis of the inner electrode.

4. An apparatus according to claim 3, wherein the outer surface of the diverter electrode is along an approximately continuous curve with the outer surface of the inner electrode over a region of the terminus of the inner electrode.

5. An apparatus according to claim 4, comprising an annular space defined between the diverter electrode and the inner electrode for providing, separately from the flow of a carrier gas, a flow of a diverting gas for diverting the ions within the at least a first ion flow path in a known fashion as the ions exit from the analyzer region between the two electrodes.

6. An apparatus for separating ions, comprising:
   a high field asymmetric waveform ion mobility spectrometer including:
   two electrodes at least one of which is for receiving an asymmetric waveform electrical signal and for producing a field between the two electrodes;
   an ion inlet;
   an analyzer region in communication with the ion inlet and defined by at least a first ion flow path through the field between the two electrodes;
   an inlet for introducing a flow of a carrier gas into the analyzer region; and, a port for providing separately from the flow of a carrier gas, a diverter gas flow for diverting the ions from the at least a first ion flow path in a known fashion relative to an ion flow path that is expected absent the diverter gas flow.

7. An apparatus according to claim 6, wherein the port is disposed between the at least a first ion flow path and a second other ion flow path within the analyzer region.

8. A method for separating ions comprising:
   a) providing an asymmetric waveform and a direct-current compensation voltage to an electrode to form an analyzer electric field within an analyzer region of a FAIMS, the field for effecting a difference in net displacement between ions in a time of one cycle of the applied asymmetric waveform for effecting a first separation of the ions and for selectively forming a subset thereof;
   b) producing ions within an ionization source and providing said produced ions into the analyzer region;
   c) providing a flow of a carrier gas for transporting said produced ions within the analyzer region through the analyzer electric field along at least a first ion flow path in a direction approximately transverse to the electric field, to effect the first separation of the ions and to selectively transmit the subset thereof; and,
   d) providing an electrical signal to a diverter electrode for producing a diverter electric field proximate an ion outlet end of the analyzer region, for diverting the selectively transmitted subset of the ions in a direction toward an ion-outlet orifice at the ion outlet end of the analyzer region in a predetermined fashion relative to the at least a first ion flow path as it would be absent diverting.

9. A method according to claim 8, wherein diverting the ions additionally comprises providing separately from the flow of a carrier gas, a flow of a diverter gas such that the diverter electric field and the flow of a diverter gas work in conjunction one with the other to divert the selectively transmitted subset of the ions in a known fashion as the ions exit from the analyzer electric field.

10. A method for separating ions comprising:
    a) providing an asymmetric waveform and a direct-current compensation voltage to an electrode to form an analyzer electric field within an analyzer region of a FAIMS, the field for effecting a difference in net displacement between ions in a time of one cycle of the applied asymmetric waveform for effecting a first separation of the ions and for selectively forming a subset thereof;
    b) producing ions within an ionization source and providing said produced ions into the analyzer region;
    c) providing a flow of a carrier gas for transporting said produced ions within the analyzer region through the analyzer electric field along at least a first ion flow path in a direction approximately transverse to the electric field, to effect the first separation of the ions and to selectively transmit the subset thereof; and,
    d) providing an electrical signal to a diverter electrode for producing a diverter electric field such that the selectively transmitted subset of the ions is diverted from the at least a first ion flow path and is attracted to a region of the diverter electrode to collide therewith.

11. A method according to claim 10, comprising providing an ion detector along at least a portion of the diverter electrode for detecting at least an ion current.

12. A method according to claim 8, wherein the selectively transmitted subset of the ions is diverted such that the ions are directed generally toward the ion-outlet orifice to pass therethrough.

13. A method according to claim 8, wherein the diverter electrode is disposed approximately between the at least a first ion flow path and a second other ion flow path within the analyzer region.

14. A method for separating ions comprising:
    a) providing an asymmetric waveform and a direct-current compensation voltage to an electrode to form an analyzer electric field within an analyzer region of a FAIMS, the field for effecting a difference in net displacement between ions in a time of one cycle of the applied asymmetric waveform for effecting a first separation of the ions and for selectively forming a subset thereof;
    b) producing ions within an ionization source and providing said produced ions into the analyzer region;
    c) providing a flow of a carrier gas for transporting said produced ions within the analyzer region through the analyzer electric field along at least a first ion flow path in a direction approximately transverse to the electric field, to effect the first separation of the ions and to selectively transmit the subset thereof;
    d) providing a first electrical signal to a first diverter electrode for producing a first diverter electric field; and,
    e) providing a second electrical signal to a second other diverter electrode for producing a second other diverter electric field, the first and second other diverter electric fields for diverting the selectively transmitted subset of the ions in a known fashion as the ions exit from the analyzer electric field, wherein the first and second other diverter electrodes are disposed on opposing sides of the at least a first ion flow path.

15. A method according to claim 14 comprising providing a second other analyzer electric field between the first and second other diverter electrodes for effecting a second other separation of the ions so as to selectively transmit a second other subset thereof, wherein the selectively transmitted subset of the ions is diverted such that a first species of ions is attracted to a region of the first diverter electrode to collide therewith and the second other subset of the ions is diverted such that a second other species of ions is attracted to a region of the second other diverter electrode to collide therewith.

16. A method according to claim 15, wherein at least one of the first and second other diverter electrodes includes an ion detector for detecting at least an ion current.

17. A method according to claim 14, comprising providing at least an electric signal to each of the diverter electrodes for displacing the selectively transmitted subset of the ions away from the diverter electrodes.

18. A method according to claim 17, wherein the ions are displaced toward an outlet orifice in communication with a low pressure region of a mass spectrometer.

19. A method for separating ions comprising:
   a) providing an asymmetric waveform and a direct-current compensation voltage to an electrode to form an analyzer electric field within an analyzer region of a FAIMS, the field for effecting a difference in net displacement between ions in a time of one cycle of the applied asymmetric waveform for effecting a first separation of the ions and for selectively forming a subset thereof;
   b) producing ions within an ionization source and providing said produced ions into the analyzer region;
   c) providing a flow of a carrier gas for transporting said produced ions within the analyzer region through the analyzer electric field along at least a first ion flow path in a direction approximately transverse to the electric field, to effect the first separation of the ions and to selectively transmit the subset thereof; and,
   d) providing, separately from the flow of a carrier gas, a diverter gas flow proximate an ion outlet end of the analyzer region, for diverting the selectively transmitted subset of the ions in a direction toward an ion-outlet orifice at the ion outlet end of the analyzer region in a predetermined fashion relative to the ion flow path as it would be absent diverting.

20. A method according to claim 19, wherein the diverter gas flow is a flow of an inert gas for directing the selectively transmitted subset of the ions in a direction of the gas flow.

21. A method according to claim 20, wherein the selectively transmitted subset of the ions is diverted such that the ions are directed to an ion detector for detecting at least an ion current.

22. A method according to claim 20, wherein the selectively transmitted subset of the ions is diverted such that the ions are directed generally toward the ion-outlet orifice to pass therethrough.

23. A method according to claim 19, wherein the diverter gas flow includes a flow of a reactive gas.

24. A method according to claim 23, wherein the reactive gas is selected to form at least a complex with at least some ions of the selectively transmitted subset of the ions within the ion flow path for effecting a second different separation of the ions.

25. A method according to claim 23, wherein the reactive gas includes at least an ionic species reactive with at least an ionic species of the selectively transmitted subset of the ions.

26. A method according to claim 25, wherein the at least an ionic species reactive with at least an ionic species of the selectively transmitted subset of the ions forms a neutral compound therewith.

27. A method according to claim 25, wherein the at least an ionic species reactive with at least an ionic species of the selectively transmitted subset of the ions forms at least a third different ionic species.

28. A method according to claim 17 wherein the ions are displaced toward an outlet orifice.

29. A method for separating ions comprising:
   a) providing an asymmetric waveform and a direct-current compensation voltage to an electrode to form an analyzer electric field for selectively transmitting an ion of interest along a first ion flow path;
   b) producing ions including the ion of interest within an ionization source;
   c) providing a flow of a carrier gas for transporting said produced ions through the analyzer electric field, to selectively transmit the ion of interest along the first ion flow path in a direction approximately transverse to the electric field;
   d) trapping the ion of interest within a known three-dimensional region of space within the analyzer electric field; and,
   e) subsequent to trapping, diverting the ion of interest from the known three-dimensional region of space toward an ion-outlet orifice for extraction therethrough.

30. An apparatus for separating ions, comprising:
   a high field asymmetric waveform ion mobility spectrometer including:
      two electrodes at least one of which is for receiving an asymmetric waveform electrical signal and for producing a field between the electrodes;
      an ion inlet;
      an analyzer region in communication with the ion inlet and defined by at least a first ion flow path between the two electrodes;
      an inlet for introducing a flow of a carrier gas into the analyzer region;
      a first ion diverter electrode separate from the two electrodes, for receiving a first electrical signal and for producing a first diverter electrical field for diverting the ions from the at least a first ion flow path in a known fashion; and,
      a second ion diverter electrode separate from the two electrodes and from the first ion diverter electrode, for receiving a second electrical signal and for producing a second diverter electrical field for diverting the ions from the at least a first ion flow path in a known fashion;
   wherein the first ion diverter electrode and the second ion diverter electrode are disposed one each on opposite sides of the at least a first ion flow path, and
   wherein the first diverter electrical field and the second diverter electrical field work in conjunction one with the other to divert the ions within the at least a first ion flow path as the ions exit from the field between the two electrodes.

31. An apparatus according to claim 7, wherein the two electrodes are concentric coaxially aligned generally cylindrical inner and outer electrode bodies forming an annular space therebetween.

32. An apparatus according to claim 31, wherein the inner electrode is provided with a terminus shaped for directing ions generally radially inward toward the central axis of the inner electrode.

33. An apparatus according to claim 32, wherein the port is defined along a region of the terminus of the inner electrode, which region is a region closest an ion-outlet orifice of the analyzer region.

34. A method for separating ions comprising:
   a) providing an asymmetric waveform and a direct-current compensation voltage to an electrode to form an analyzer electric field, the field for effecting a difference in net displacement between ions in a time of one cycle of the applied asymmetric waveform for effecting a first separation of the ions and for selectively forming a subset thereof;
   b) producing ions within an ionization source;
   c) providing a flow of a carrier gas for transporting said produced ions through the analyzer electric field along at least a first ion flow path in a direction approximately transverse to the electric field, to effect the first separation of the ions and to selectively transmit the subset thereof; and, d) providing an electrical signal to a diverter electrode for producing a diverter electric field; and, diverting the selectively transmitted subset of the ions in a predetermined fashion relative to the at least a first ion flow path as it would be absent diverting e) providing separately from the flow of a carrier gas, a flow of a diverter gas such that the diverter electric field and the flow of a diverter gas work in conjunction one with the other to divert the selectively transmitted subset of the ions in a known fashion as the ions exit from the analyzer electric field.

* * * * *